(12) United States Patent
Suter et al.

(10) Patent No.: US 10,820,964 B2
(45) Date of Patent: Nov. 3, 2020

(54) DRILL GUIDE HAVING A LIMIT STOP

(75) Inventors: Edmund Suter, Niederdorf (CH);
Patrick Streff, Weil am Rhein (DE);
Steffen Kuehne, Moehlin (CH)

(73) Assignee: STRAUMANN HOLDING AG, Basel (CH)

( * ) Notice: Subject to any disclaimer, the term of this patent is extended or adjusted under 35 U.S.C. 154(b) by 1513 days.

(21) Appl. No.: 12/674,035

(22) PCT Filed: Aug. 20, 2008

(86) PCT No.: PCT/EP2008/006823
§ 371 (c)(1),
(2), (4) Date: Sep. 7, 2010

(87) PCT Pub. No.: WO2009/024328
PCT Pub. Date: Feb. 26, 2009

(65) Prior Publication Data
US 2011/0046631 A1 Feb. 24, 2011

(30) Foreign Application Priority Data

Aug. 22, 2007 (EP) .................................... 07016398
Jul. 3, 2008 (EP) .................................... 08011996

(51) Int. Cl.
*A61C 1/08* (2006.01)
*A61C 8/00* (2006.01)
*A61C 3/00* (2006.01)

(52) U.S. Cl.
CPC ............ *A61C 1/084* (2013.01); *A61C 8/0089* (2013.01); *A61C 3/00* (2013.01)

(58) Field of Classification Search
CPC ....... A61C 1/084; A61C 1/085; A61C 1/0089; A61C 1/082; A61B 17/17; B25B 13/04; B25B 13/08; B25B 13/56
USPC ...................... 433/72, 75, 76; 434/203, 270; 623/11.11, 901; 606/96–98; 81/125.1, 81/177.1
See application file for complete search history.

(56) References Cited

U.S. PATENT DOCUMENTS

| | | | |
|---|---|---|---|
| 1,503,084 A * | 7/1924 | Bain ....................... | B25B 13/08 81/125.1 |
| 5,015,183 A | 5/1991 | Fenick | |
| 5,133,660 A | 7/1992 | Fenick | |

(Continued)

FOREIGN PATENT DOCUMENTS

DE 299 09 616 U1 6/1999
DE 20 2006 004 954 U1 7/2006
(Continued)

OTHER PUBLICATIONS

International Search Report in corresponding PCT/EP2008/006823.

*Primary Examiner* — Matthew M Nelson
(74) *Attorney, Agent, or Firm* — Oliff PLC

(57) ABSTRACT

The present invention relates to a drill guide (1) for use in the dental field. It comprises a grip (5) and at least two guide sleeves (10) arranged on the grip, the grip (5) having a top face (25) and an underside (30) and the underside (30) of the grip being intended to bear at least partially on a drill jig. The at least two guide sleeves (10) protrude from the underside (30) of the grip, and at least one limit stop (55), which is an axial continuation of one of the at least two guide sleeves (10), protrudes from the top face (25) of the grip.

27 Claims, 4 Drawing Sheets

(56) References Cited

U.S. PATENT DOCUMENTS

| | | | | |
|---|---|---|---|---|
| 5,302,122 A | * | 4/1994 | Milne | A61C 1/084 433/173 |
| 5,320,529 A | | 6/1994 | Pompa | |
| 5,557,992 A | * | 9/1996 | Macor | B25B 13/04 81/124.4 |
| 5,888,034 A | * | 3/1999 | Greenberg | A61B 17/02 408/115 R |
| 5,915,962 A | * | 6/1999 | Rosenlicht | A61C 1/084 433/76 |
| 5,954,769 A | | 9/1999 | Rosenlicht | |
| 6,062,856 A | * | 5/2000 | Sussman | A61C 1/084 433/76 |
| 6,290,497 B1 | * | 9/2001 | Di Emidio | A61C 1/084 433/76 |
| 6,319,000 B1 | * | 11/2001 | Brånemark | A61C 1/084 433/173 |
| 7,093,520 B2 | * | 8/2006 | Tuanmu | B25B 13/04 81/177.1 |
| 7,201,086 B2 | * | 4/2007 | Hansen | B25B 13/04 81/124.5 |
| D562,654 S | * | 2/2008 | Yang | D8/27 |
| 7,942,668 B2 | * | 5/2011 | Brajnovic | A61C 1/084 433/75 |
| 2003/0022131 A1 | * | 1/2003 | Kangasniemi | A61C 3/00 433/147 |
| 2003/0157457 A1 | | 8/2003 | Blacklock | |
| 2004/0020329 A1 | * | 2/2004 | Boman | B25B 13/06 81/125.1 |
| 2004/0142300 A1 | | 7/2004 | Aravena | |
| 2004/0219477 A1 | | 11/2004 | Harter | |
| 2004/0219479 A1 | | 11/2004 | Malin et al. | |
| 2004/0219481 A1 | | 11/2004 | Malin et al. | |
| 2005/0034572 A1 | * | 2/2005 | Hsien | B25B 13/461 81/177.2 |
| 2005/0100860 A1 | * | 5/2005 | Kameli | A61C 3/00 433/144 |
| 2005/0170311 A1 | * | 8/2005 | Tardieu | A61C 1/084 433/76 |
| 2005/0282106 A1 | * | 12/2005 | Sussman | A61C 1/084 433/76 |
| 2006/0225235 A1 | * | 10/2006 | Mortimer | A46B 5/0012 15/167.2 |
| 2006/0240378 A1 | | 10/2006 | Weinstein et al. | |
| 2006/0240379 A1 | * | 10/2006 | Weinstein | A61B 5/103 433/76 |
| 2006/0263743 A1 | | 11/2006 | Tedesco | |
| 2007/0077532 A1 | | 4/2007 | Harter | |
| 2007/0270771 A1 | * | 11/2007 | Ralph et al. | A61B 17/1635 604/317 |
| 2007/0281270 A1 | * | 12/2007 | Brajnovic | A61C 1/084 433/72 |
| 2008/0064005 A1 | | 3/2008 | Meitner | |
| 2008/0124672 A1 | * | 5/2008 | Sussman | A61C 1/084 433/76 |
| 2008/0166681 A1 | | 7/2008 | Weinstein et al. | |
| 2009/0325122 A1 | * | 12/2009 | Brajnovic | A61C 1/084 433/75 |

FOREIGN PATENT DOCUMENTS

| | | |
|---|---|---|
| DE | 10 2005 023 028 A1 | 11/2006 |
| EP | 1894539 A1 | 3/2008 |
| EP | 2060240 A2 | 8/2009 |
| WO | WO 94/00073 A1 | 1/1994 |
| WO | WO 9400073 A1 * | 1/1994 |
| WO | WO 97/43981 A1 | 11/1997 |
| WO | WO 97/49351 | 11/1997 |
| WO | WO 03/071972 A1 | 9/2003 |
| WO | WO 2005/053566 A1 | 6/2005 |
| WO | WO 2006/014130 A1 | 2/2006 |
| WO | WO 2006/130067 A1 | 12/2006 |
| WO | WO 2007/067105 A1 | 6/2007 |
| WO | WO 2007/077223 A1 | 7/2007 |
| WO | WO 2007/079775 A1 | 7/2007 |
| WO | WO 2007/104842 A1 | 9/2007 |
| WO | WO 2008/089885 A1 | 7/2008 |

* cited by examiner

DRILL GUIDE HAVING A LIMIT STOP

The present invention relates to a drill guide having a limit stop for use in the dental field.

To achieve a prosthetically optimized implant axis, a drill jig is often used, e.g. an OP jig or CT splint. Drill jigs are known for guiding dental implant drills for preparing the jaw bone and are intended to receive one or more dental implants. Drill jigs of this kind are modeled manually or manufactured with the aid of a computer (CAM). They have drill holes that serve to guide a dental implant drill or the implant during a surgical intervention. Standardized metal drill sleeves (hereinafter standard drill sleeves) are often incorporated into the drill jigs, e.g. polymerized in or pressed in, so as to increase the precision of the drilling operations. During a surgical intervention, the dental implant drill is guided by such a sleeve. The drill jig thus serves to ensure that the drilling is carried out precisely in accordance with the optimal implant axes that have been determined at the planning stage.

In most implantation methods, the drilling is carried out in several steps. For example, a first drilling step is carried out with a pilot drill of small diameter, followed by a drilling step using a twist drill having the final diameter of the implant that is to be inserted. Depending on the method used, other drills with intermediate diameters or other cutting geometries may also be needed.

To apply this method, suitable reduction sleeves that define the diameter of the drilling are fitted into the holes or standard drill sleeves of the drill jigs.

The fact that the reduction sleeves are also exchanged during the treatment, and that they typically have diameters of less than 6 mm, results in handling difficulties and even the risk of aspiration by the patient.

A further problem is that the drill must not penetrate too deeply into the bone, since otherwise the nerves may be damaged.

Reduction sleeves with grip-like extensions are known from WO 06/130067. The step-wise reduction in diameter is achieved by several reduction sleeves being stacked one inside another.

WO 06/014130 describes a reduction sleeve which is connected to a grip via a ball-and-socket hinge so as to be able to address different space situations in the patient's mouth.

WO 97/49351 discloses an implant-supported device for guiding a drill, with an auxiliary insert from which two reduction sleeves of identical diameter protrude and are held in a parallel position via a flat connection.

U.S. Pat. No. 5,888,034 describes a drill guide with a guide sleeve which is mounted on a grip and whose length can be adjusted like a telescope. Further reduction sleeves are present in the grip. The manual adjustment of the desired drilling depth is time-consuming and prolongs the treatment time. Moreover, the described drill guide is difficult to sterilize.

WO 94/00073 describes a securing device containing a drill guide that is movable relative to the securing device. To fix the securing device, a pilot bore is needed, which cannot be drilled in a guided manner.

The object of the present invention is to make available an aid that is easy to handle and that can be used to reduce the diameter of the holes in drill jigs and at the same time prevents the drill from penetrating too deeply. The object is achieved by a drill guide with the features of claim 1. Other preferred embodiments form the subject matter of claims 2 through 17.

By means of the drill guide according to the invention, it is possible to work with a large number of different drills in one drill jig, without the need for complicated handling of small reduction sleeves. At the same time, it is possible to fix the maximum drilling depth since further penetration of the drill is prevented by a limit stop surface on the top face of an at least one limit stop or on the top face of the grip. By simply turning the drill guide according to the invention, the surgeon is able to insert a guide sleeve of a specific internal diameter and a specific drilling depth into the drill jig. He then takes the next drill guide, which has a greater internal diameter, and inserts it into the drill jig such that he again obtains an identical drilling depth as with the first drill guide. This procedure is repeated until a hole with the desired diameter and depth is obtained. A set composed of four drill guides with different internal diameters is normally sufficient to obtain a standard implant bore.

The drill guide according to the invention comprises a grip and at least two guide sleeves which each have an upper end and a lower end. The grip has a top face and an underside. The at least two guide sleeves protrude from the underside of the grip, i.e. they are arranged on the same side of the grip. At least one limit stop, which is an axial continuation of one of the at least two guide sleeves, protrudes from the top face of the grip. Such a limit stop has a height of a few millimeters, which means that a drill guide according to the invention can also be easily used in a difficult space situation in the patient's mouth. It is important that the two guide sleeves are arranged on the same side of the grip so as to permit optimal use of the drill guide also in the area of the molars. This also ensures that the operator's view is limited only minimally by the drill guide according to the invention.

A limit stop which protrudes from the top face of the grip and is an axial continuation of a guide sleeve, and further limit stops that likewise protrude from the top face of the grip and form an axial continuation of a guide sleeve, or the top face of the grip, immediately next to the top end of the guide sleeve, serve as a limit stop surface for the drilling tool, i.e. they ensure that the surgeon does not drill too deeply. This avoids damage to nerves during drilling. Since the height of the limit stop surfaces of the at least one limit stop is different from the height of the limit stop surface of a further limit stop or the height of the limit stop surface on the top face of the grip, the operator has the choice between different drilling depths.

The grip can be rigid or shapeable. It can also be flat, semicircular or round. In order to ensure better sterilization, the surface is preferably smooth. The length of the drill guide according to the invention is chosen such that the potential drilling sites in the jaw bone can be reached and the grip can generally be grasped outside the oral cavity. The preferred grip of the drill guide according to the invention has a length of between 5 and 12 cm.

At least part of the underside of the grip is intended to bear on a drill jig. In this way, the dentist is provided with still greater stability during drilling, such that the drill cannot slip. This bearing part preferably bears on the drill jig directly adjacent to the guide sleeve. This can, for example, be the radially outward continuation of the guide sleeve on the grip or can also be an endpiece of the grip.

The guide sleeves, which protrude from the underside of the grip, have an upper end and a lower end. The upper end is directed toward the grip, while the lower end is arranged on the side directed away from the underside of the grip. It is possible to produce the guide sleeves separately and to insert them into the grip, in which case the upper end of the guide sleeve is connected to the grip. However, it is preferable for the drill guide to be made in one piece, in order to ensure better sterilization. The guide sleeves are cylindrical and have such an external diameter that they fit exactly into the drill holes of the drill jig or into the corresponding standard drill sleeves. The internal diameter is adapted to the diameters of the drills.

The height of the guide sleeves and of the limit stop surface of the at least one limit stop or the limit stop surface of the top face of the grip determine, together with the geometry of the drilling tool, the precision and the depth of the drilling operation. Long guide sleeves increase the precision of the drill guide, but at the same time also increase the overall height of those parts of the drill jig, drill guide and drilling tool bearing on one another. Satisfactory results are achieved with guide sleeves with a height starting from 5 mm in the cylindrical area. Ideally, however, the height is not more than 10 mm.

In a preferred embodiment, the drill guide has exactly two guide sleeves. These are preferably each arranged in the end area of the grip. In this way, the guide sleeves are at a maximum distance from each other, which has the effect that the second guide sleeve does not obstruct the use of the first guide sleeve.

It is particularly preferable if exactly one limit stop, which is an axial continuation of one of the two guide sleeves, protrudes from the top face of the grip. Here, the operator accordingly has the choice between two drilling depths. He either chooses the side of the drill guide which has a guide sleeve and a limit stop or else he chooses the side which has a guide sleeve and in which the top face of the grip lying at the upper end of this guide sleeve serves as a limit stop surface. In the first case, the drill will penetrate less deeply into the bone than in the second case, since the limit stop surface of the limit stop meets the drill earlier than the limit stop surface of the grip. The operator is thus easily able to fix the drilling depth without the instrument, i.e. the drill guide, having to be given a defined setting by screwing or rotating prior to use. In this embodiment, the two guide sleeves ideally have an identical internal diameter. The latter is preferably chosen from the group consisting of 2.2 mm, 2.8 mm, 3.5 mm and 4.2 mm.

Alternatively, instead of the limit stop surface of the grip, it is also possible for the drill guide to have a second limit stop, which is an axial continuation of the second guide sleeve. In this case, the height of the first limit stop in the axial direction is different from the height of the second limit stop. Ideally, the height of the first limit stop is in the range of 1 to 2 mm and the height of the second limit stop is in the range of 3 to 4 mm. In this embodiment too, the two guide sleeves ideally have an identical internal diameter. The latter is preferably chosen from 2.2 mm, 2.8 mm, 3.5 mm and 4.2 mm.

Instruments used in dental implantology must in particular take into account the dimensions and physiology of the patient's mouth. If two guide sleeves are connected via a grip, they should be arranged in such a way that the second end of the drill guide, not situated in the drill jig, does not impede the use of the first guide sleeve to be fitted in the drill jig. Besides the fact that the guide sleeves are arranged on the same side of the grip, it is of advantage for the grip to be angled. In a preferred embodiment, for example, both ends of the grip are S-shaped, such that the grip has a bridge-like shape. In this way, the patient's tongue is given sufficient space under it and is kept away from the drilling site by the grip lying above it. In addition, the drill guide is preferably shaped in such a way that it can also be used without any problem anywhere in a partially toothed jaw. Therefore, the S-shaped angle in the grip should be as close as possible to the guide sleeve. At the same time, sufficient space for the headpiece of the customary dental drilling devices must remain above the guide sleeve. The guide sleeves of the present invention are preferably parallel to one another on the grip, since in this way the overall height of the drill guide remains smaller. It is also conceivable, however, for the grip to be angled, this angled configuration preferably being arranged in the middle part of the grip. Such an angled configuration means that the guide sleeves are also at an angle to one another.

When using a plurality of drill guides according to the invention, a coding arrangement can be employed. The color codes often used on the drills can be adopted for the drill guides and can be applied at a suitable location, for example on the grip near the corresponding guide sleeve. A coding arrangement can also give the operator information concerning the drilling depth, i.e. the height of the limit stop. Alternatively, the guide sleeve itself can be painted the appropriate color.

Operating instruments used in surgery must be able to be reliably cleaned and sterilized. For this reason, one-part drill guides with smooth and accessible surfaces are preferred. Particular preference is given to one-part drill guides produced in one piece, since they do not have any connection points. However, multi-part drill guides with connection points that do not form gaps, and that are easy to clean, are also conceivable. It is also advantageous, during treatment, to be able to use operating instruments that do not have to be adjusted, modified or exchanged. The drill guides according to the invention meet these requirements. They have no undercuts and are easy to sterilize.

The preferred materials from which the drill guides of the present invention are made include stainless steel, titanium or other metal alloys customarily used in surgery. To increase the useful life of the drill guide, parts of the drill guide, for example the guide sleeves, can additionally be treated by surface-hardening techniques. One expedient technique for hardening of stainless steel is Kolsterizing. In one embodiment, the material is chosen such that the grip can be bent by hand, the result being that the operator can shape it in such a way that it is adapted as best possible to the spatial conditions in the mouth.

The drill guide according to the invention can be made available in sets together with drill jigs. The drill jigs can optionally contain standard drill sleeves. The external diameter of the guide sleeves of the drill guide should match the internal diameter of the drill holes of the drill jig and the internal diameter of the standard drill sleeve. It is likewise possible for several drill guides each having different internal diameters to be made available in one set. Such a set ideally comprises four drill guides, with each drill guide having two guide sleeves, which are of identical internal diameter, and a limit stop, which is an axial continuation of a guide sleeve. Particularly preferably, the guide sleeves of the first drill guide have an internal diameter of 2.2 mm, the guide sleeves of the second drill guide have an internal diameter of 2.8 mm, the guide sleeves of the third drill guide have an internal diameter of 3.5 mm, and the guide sleeves of the fourth drill guide have an internal diameter of 4.2 mm.

The drill guide according to the invention is explained in greater detail below on the basis of preferred embodiments in FIGS. 1 to 4.

Figure 1:
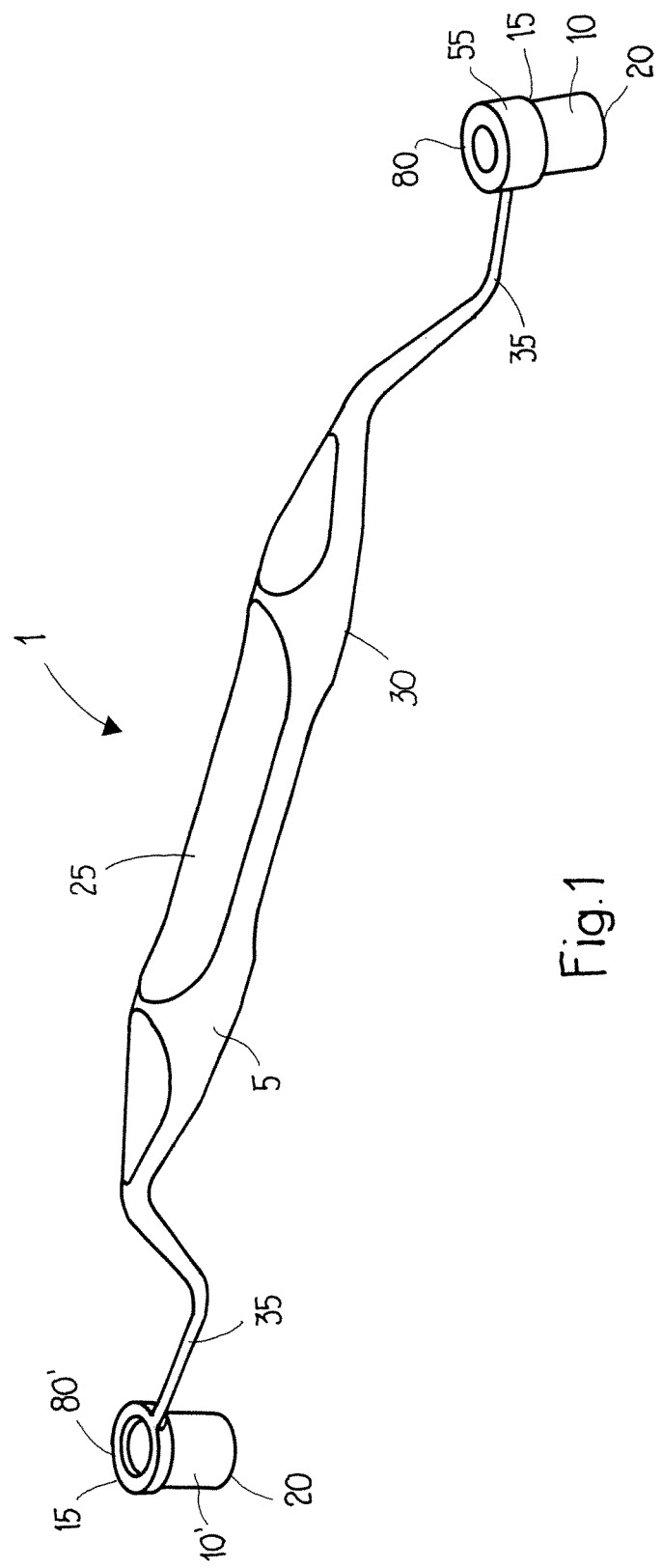
FIG. 1 shows a drill guide according to the invention with two guide sleeves and a limit stop.

A drill guide 1 for use in the dental field is depicted in FIG. 1. The drill guide 1 has a one-part grip 5 and at least two guide sleeves 10, 10' each with an upper end 15 directed toward the grip, and an end 20 directed away from the grip. The grip has a top face 25 and an underside 30, and a part 35 of the underside 30 is intended to bear on the drill jig. This part 35, which is in direct proximity to the guide sleeve 10, ensures that the drill guide sits on the drill jig. The at least two guide sleeves 10 protrude from the underside 30 of the grip and are each arranged at the end of the grip. By virtue of the fact that the guide sleeves are oriented in the same direction, i.e. are arranged on the same side of the grip, it is possible to leave as much room as possible in the oral cavity for the tongue and to allow the patient a comfortable angle of opening of the mouth during the drilling procedure. To ensure that the drill guide, when fitted into the drill jig, does not as a whole extend too far into the oral cavity and does not have a disadvantageous overall height, the grip preferably has a double angle or an S-shaped portion, such that the drill guide has a bridge-like shape. The S-shaped angle is as close as possible to the guide sleeve. A limit stop 55, which is an axial continuation of one of the two guide sleeves 10, protrudes from the top face 25 of the grip. The top face of this limit stop serves as a limit stop surface 80 for the drill, in order to ensure that the latter does not penetrate too deeply into the bone. There is no limit stop protruding from the top face 25 of the grip opposite the second guide sleeve 1". Here, the top face of the grip serves as a limit stop surface 80' for the drill. In this way, a different drilling depth is fixed depending on which guide sleeve is inserted into the drill jig.

The drill guide shown in FIG. 1 is made in one piece and has no undercuts. The one-piece configuration means that there are no connections between individual components, which connections may possibly make it more difficult to sterilize the drill guide. It is also conceivable, however, for the drill guide according to FIG. 1 to be made in several pieces, by producing the guide sleeves separately and connecting them to the grip.

Figure 2B:
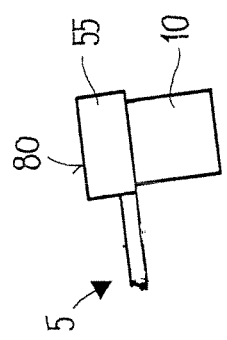
FIGS. 2a and 2b show details of the drill guide shown in FIG. 1.
Figure 2A:
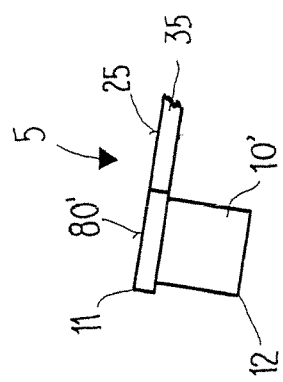

FIGS. 2a and 2b show a detail of the drill guide according to FIG. 1. FIG. 2a shows the second guide sleeve 10', which is arranged on the underside of the grip 5. The guide sleeve 10' has an upper end 11 and a lower end 12. The upper end 12 corresponds to the top face 25 of the grip and serves as a limit stop surface 80' for the drill. FIG. 2b shows the first guide sleeve 10, which is arranged on the underside of the grip 5. A limit stop 55, which is an axial continuation of the guide sleeve 10, protrudes from the top face of the grip. The top face of the limit stop 55 serves as a limit stop surface 80 for the drill.

Figure 3B:
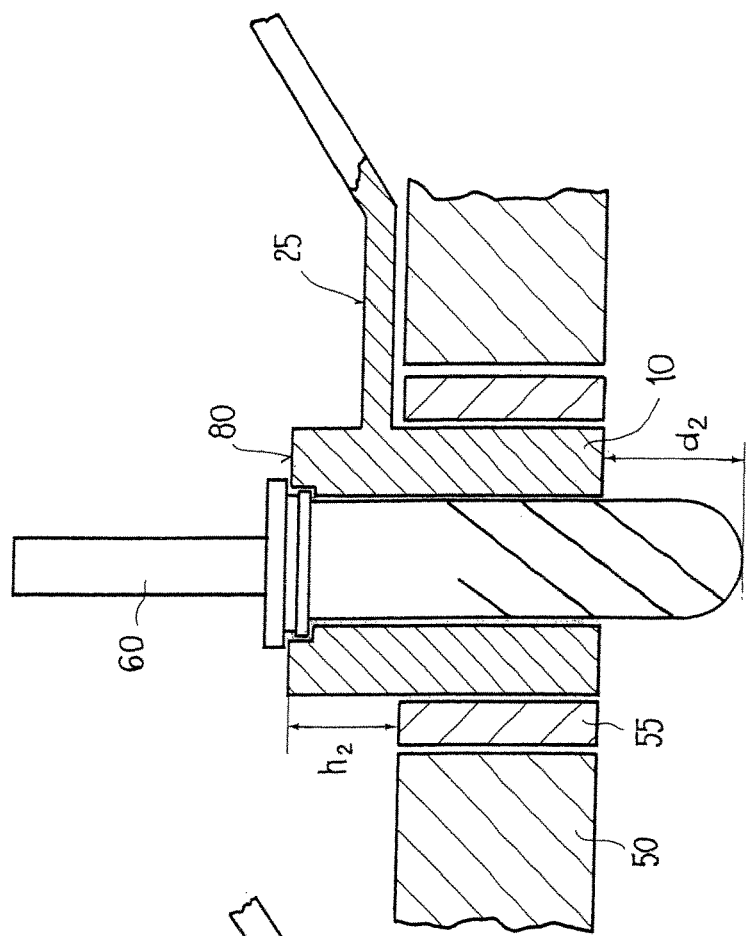
FIGS. 3a and 3b show the drill guide from FIG. 1 in a drill jig.
Figure 3A:
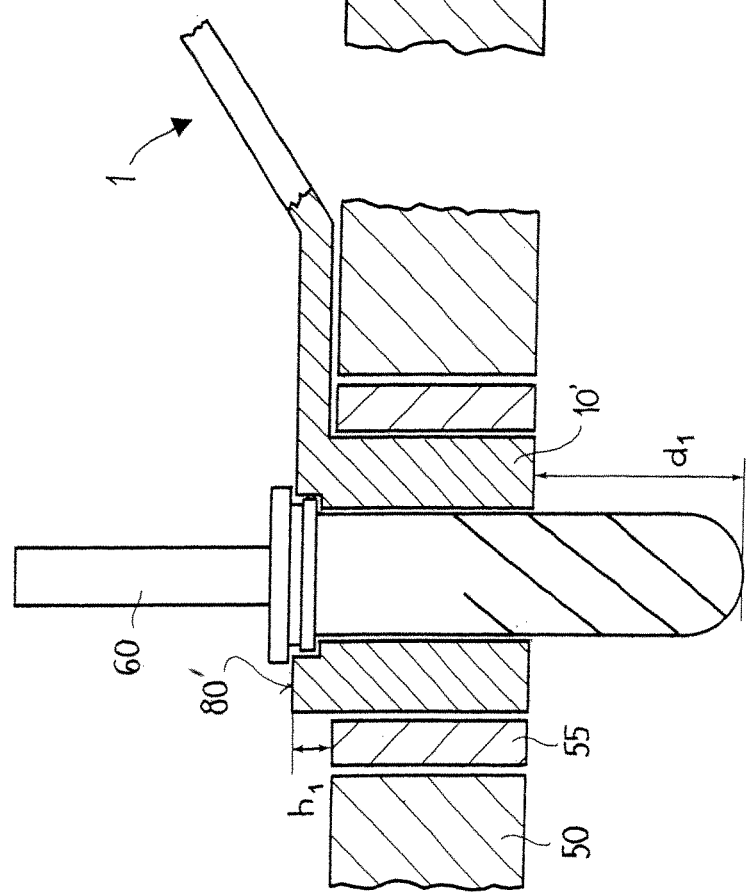

FIGS. 3a and 3b show a section through a drill jig 50 with a standard drill sleeve 55, which contains the drill guide 1 according to FIG. 1. In FIG. 3a, the drill guide is inserted into the standard drill sleeve 55 such that the drill 60 strikes against the top face of the grip, that is to say the limit stop surface 80', which thus acts as a drill stop. The drill 60 is guided through the guide sleeve 10 of the drill guide. In FIG. 3b, the drill guide is inserted into the standard drill sleeve such that the drill 60 strikes against the limit stop surface 80 of the limit stop 55. The limit stop surface 80 of the limit stop 55, which protrudes from the top face 25 of the grip and is an axial continuation of the guide sleeve 10, is spaced apart from the top face of the drill jig by the height h2. The limit stop surface 80, which corresponds to the top face of the grip, is spaced apart by the height h1 from the top face of the drill jig. The difference h2−h1 corresponds to the difference in drilling depth d2−d1 that is obtained depending on whether the guide sleeve without limit stop or the guide sleeve with limit stop is used during the drilling.

Figure 4:
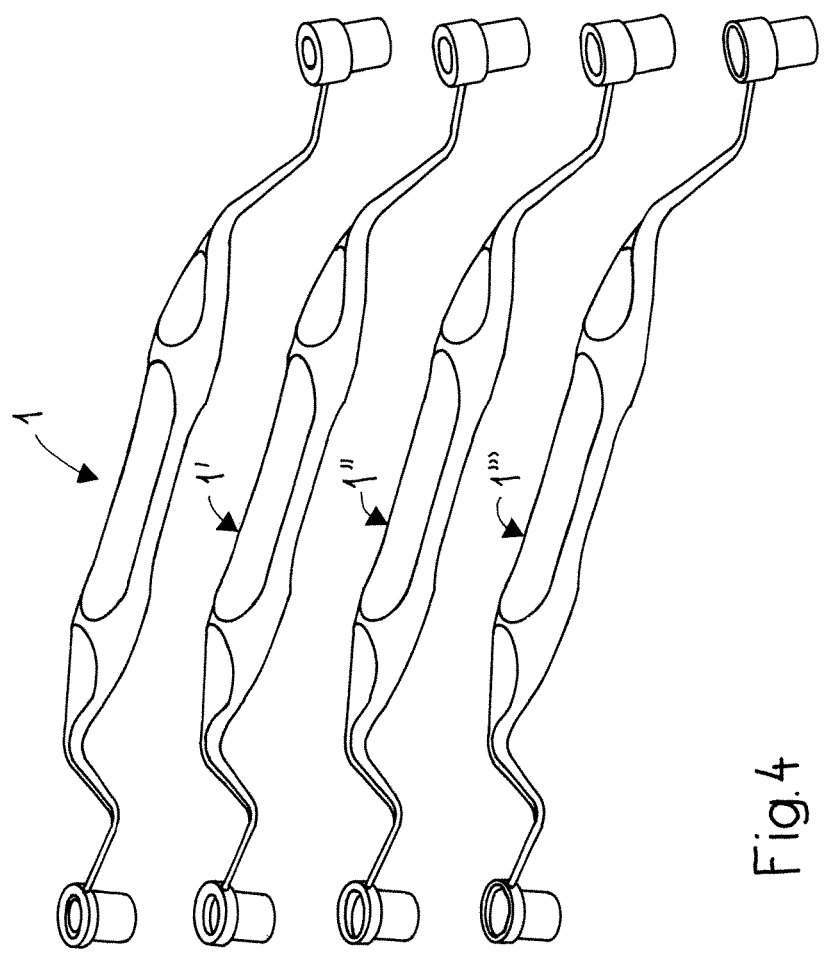
FIG. 4 shows a set with four different drill guides.

FIG. 4 shows a set with four drill guides according to the invention. The drill guides 1, 1', 1" and 1'" differ from one another in that each drill guide has guide sleeves with a different internal diameter. That is to say, the guide sleeves of the first drill guide 1 have an identical internal diameter but differ from each other in that, on one side, a limit stop is situated on the top face of the grip and forms an axial continuation of a guide sleeve. With the first drill guide, the operator can therefore carry out drilling with a defined drill diameter but has two drilling depths to choose from. Each of these drill guides 1, 1', 1" and 1'" has two guide sleeves, of identical internal diameter, and a limit stop, which is an axial continuation of a guide sleeve. The limit stops of all the drill guides are the same height. The operator is thus able to keep the drilling depth constant and continuously widen the drilling diameter. Particularly preferably, the guide sleeves of the first drill guide have an internal diameter of 2.2 mm, the guide sleeves of the second drill guide 1' have an internal diameter of 2.8 mm, the guide sleeves of the third drill guide 1" have an internal diameter of 3.5 mm, and the guide sleeves of the fourth drill guide 1'" have an internal diameter of 4.2 mm.

The invention claimed is:

1. A drill guide for use with a drill jig in the dental field, comprising:
    an elongated grip having opposite ends, the grip configured to be held in a hand outside an oral cavity of a patient during drilling, wherein an entirety of the grip can be bent by hand;
    two drill guide sleeves, each fixed to the grip, one at each end of the grip;
    the grip having an underside and a top face, the underside having a bearing part adjacent each guide sleeve configured to bear against a drill jig to stabilize the drill guide;
    each guide sleeve extending a same fixed distance from the underside of the grip;
    each guide sleeve extending a different distance from the top face of the grip to form a limit stop of a different height to provide a different drilling depth limit when the guide sleeve is inserted in a drill hole of a drill jig.

2. The drill guide as claimed in claim 1, wherein the drill guide is made in one piece.

3. The drill guide as claimed in claim 1, wherein the drill guide is made in several pieces.

4. The drill guide as claimed in claim 1, wherein the grip has an S-shaped portion near the guide sleeve.

5. The drill guide as claimed in claim 4, wherein the S-shaped portion is curved.

6. The drill guide as claimed in claim 1, wherein the guide sleeves are parallel to one another in the axial direction.

7. The drill guide as claimed in claim 1, wherein the guide sleeves are at an angle to one another in the axial direction.

8. The drill guide as claimed in claim 1, made of stainless steel.

9. The drill guide as claimed in claim 1, wherein the internal diameter of the at least two guide sleeves is identical.

10. The drill guide as claimed in claim 9, wherein the drill guide has two guide sleeves of identical internal diameter, the internal diameter being of a size chosen from the group consisting of 2.2 mm, 2.8 mm, 3.5 mm and 4.2 mm.

11. A set comprising a drill jig with drill holes and a drill guide as claimed in claim 1, wherein the external diameters of the guide sleeves match the diameters of the drill holes in the drill jig.

12. A set comprising a drill jig, with drill holes containing standard drill sleeves, and a drill guide as claimed in claim 1, wherein the external diameters of the guide sleeves match the internal diameters of the standard drill sleeves contained in the drill holes of the drill jig.

13. A set comprising at least two drill guides as claimed in claim 9, wherein all the drill guides have guide sleeves of different internal diameters.

14. The set as claimed in claim 13, comprising four drill guides.

15. A set comprising a drill jig with drill holes and a drill guide for use in the medical field, the drill guide comprising:
   an elongated grip having opposite ends, the grip configured to be held in a hand outside an oral cavity of a patient during drilling; and
   two drill guide sleeves, each fixed to the grip, one at each end of the grip;
   the grip having an underside and a top face, the underside having a bearing part adjacent each guide sleeve configured to bear against a drill jig to stabilize the drill guide;
   each guide sleeve extending a same fixed distance from the underside of the grip;
   each guide sleeve extending a different distance from the top face of the grip to form a limit stop of a different height to provide a different drilling depth limit when the guide sleeve is inserted in a drill hole of a drill jig;
wherein:
   the external diameters of the guide sleeves match the diameters of the drill holes in the drill jig; and
   the drill jig is formed of a single, indivisible structure.

16. The set as claimed in claim 15, comprising at least two drill guides, wherein all the drill guides have guide sleeves of different internal diameters.

17. The set as claimed in claim 16, comprising four drill guides.

18. The set as claimed in claim 15, wherein the drill guide is made in one piece.

19. The set as claimed in claim 15, wherein the drill guide is made in several pieces.

20. The set as claimed in claim 15, wherein the grip has an S-shaped portion near the guide sleeve.

21. The set as claimed in claim 20, wherein the S-shaped portion is curved.

22. The set as claimed in claim 15, wherein the grip can be bent by hand.

23. The set as claimed in claim 15, wherein the guide sleeves are parallel to one another in the axial direction.

24. The set as claimed in claim 15, wherein the guide sleeves are at an angle to one another in the axial direction.

25. The set as claimed in claim 15, wherein the drill guide is made of stainless steel.

26. The set as claimed in claim 15, wherein the internal diameter of the two guide sleeves is identical.

27. The set as claimed in claim 26, wherein the drill guide has two guide sleeves of identical internal diameter, the internal diameter being of a size chosen from the group consisting of 2.2 mm, 2.8 mm, 3.5 mm and 4.2 mm.

* * * * *